United States Patent
Linares (10) Patent No.: US 8,051,699 B2
(45) Date of Patent: Nov. 8, 2011

(54) ABRASIVE WEAR TESTING MACHINE WITH CYCLE PROGRAMMABILITY AND VARIABLE FORCE APPLICATION

(75) Inventor: Miguel A. Linares, Bloomfield Hills, MI (US)

(73) Assignee: Linares Medical Devices, LLC, Auburn Hills, MI (US), part interest ( * ) Notice: Subject to any disclaimer, the term of this patent is extended or adjusted under 35 U.S.C. 154(b) by 125 days.

(21) Appl. No.: 12/612,459

(22) Filed: Nov. 4, 2009

(65) Prior Publication Data
US 2010/0122567 A1   May 20, 2010

Related U.S. Application Data

(60) Provisional application No. 61/114,621, filed on Nov. 14, 2008.

(51) Int. Cl.
*G01N 3/06* (2006.01)
*G01N 19/02* (2006.01)

(52) U.S. Cl. .............................................. 73/7
(58) Field of Classification Search ...................... 73/7
See application file for complete search history.

(56) References Cited

U.S. PATENT DOCUMENTS

| | | | |
|---|---|---|---|
| 3,834,219 A * | 9/1974 | Brauer | 73/7 |
| 3,913,377 A | 10/1975 | Lindeman | |
| 4,936,135 A | 6/1990 | Annis et al. | |
| 4,939,922 A | 7/1990 | Smalley et al. | |
| 4,958,511 A | 9/1990 | Marcus | |
| 5,140,242 A | 8/1992 | Doran et al. | |
| 5,377,525 A | 1/1995 | Hutchinson et al. | |
| 5,795,990 A | 8/1998 | Gitis et al. | |
| 6,167,745 B1 | 1/2001 | Hamer et al. | |
| 6,230,544 B1 | 5/2001 | Matsubara et al. | |
| 6,247,356 B1 | 6/2001 | Merck, Jr. et al. | |
| 6,401,058 B1 | 6/2002 | Akalin et al. | |
| 6,418,776 B1 | 7/2002 | Gitis et al. | |
| 6,581,437 B2 | 6/2003 | Chrystall et al. | |
| 7,000,451 B1 | 2/2006 | Wegand et al. | |
| 7,013,705 B2 | 3/2006 | Wortmann et al. | |
| 7,272,969 B2 | 9/2007 | Shinohara et al. | |
| 7,621,187 B2 | 11/2009 | Chalmers | |
| 2002/0062678 A1* | 5/2002 | Ahn et al. | 73/9 |

FOREIGN PATENT DOCUMENTS

KR  100866760 A  9/2008

* cited by examiner

*Primary Examiner* — Lisa Caputo
*Assistant Examiner* — Jamel Williams
(74) *Attorney, Agent, or Firm* — Gifford, Krass, Sprinkle, Anderson & Citkowski, P.C.

(57) ABSTRACT

An abrasive wear testing machine exhibiting a support surface upon which is dynamically supported a tray to which a wear piece is secured. A tool bit is supported by a vertically displaceable and weight supporting bracket in a fixed and downward load applied fashion against the wear piece, such that the tray is reciprocated a selected number of cycles to determine a wear profile exerted upon the wear piece by the tool bit. The bracket is configured so that end located receiving channels are each seatingly engaged upon upwardly extending hydraulic lifts secured to the support surface, with a plurality of free weights arranged upon the hydraulic lifts.

23 Claims, 7 Drawing Sheets

ABRASIVE WEAR TESTING MACHINE WITH CYCLE PROGRAMMABILITY AND VARIABLE FORCE APPLICATION

CROSS REFERENCE TO RELATED APPLICATIONS

The present application claims priority of U.S. Provisional Patent Application Ser. No. 61/114,621 filed Nov. 14, 2008.

FIELD OF THE INVENTION

The present invention is an abrasive wear testing machine, such as which incorporates gravity exerting weights or other type of fluid pressure induced forces. At least one abrading (tool) bit is arranged upon an underside of the overhead weighting and is exerted downwardly against any plurality of individual test pieces which are in turn being mounted within a supported tray, and which is caused to reciprocally displace upon a table top surface of the machine so that the tool bit abradingly engages each of a plurality of wear pieces (or material work-pieces) this in order to determine wear characteristics over a specified number of displacement cycles/iterations.

DESCRIPTION OF THE BACKGROUND ART

In materials science, wear is defined as the erosion of material from a solid surface such as by the action of another surface. It is related to surface interactions and more specifically the removal of material from a surface as a result of mechanical action. The need for mechanical action, in the form of contact due to relative motion, is an important distinction between mechanical wear and other processes with similar outcomes. Various testing and diagnostic machines are known in the art and which operate to measure a given rate or quantum of wear of a test specimen or material over a determined number of cycles and in response to load conditions and other input parameters.

SUMMARY OF THE INVENTION

The present invention discloses an abrasive wear testing machine exhibiting a support surface upon which is dynamically supported a tray to which a wear piece is secured. A tool bit is supported by a vertically displaceable and weight supporting bracket (this defined to include both free weights as well as the incorporation of pressure inducing cylinders) in a fixed and downward load applied fashion against the wear piece, such that the tray is reciprocated a selected number of cycles to determine a wear profile exerted upon the wear piece by the tool bit.

The bracket exhibits first and second end-mounted and downwardly pressure exerting cylinders and is configured so that end located receiving channels are each seatingly engaged upon upwardly extending hydraulic lifts secured to the support surface, with a plurality of free weights arranged upon the hydraulic lifts. Additional features associated with the lifts include a reverse and upwardly retracting drive arm, these cooperating to upwardly displace the weight supporting bracket such that its underneath mounted bit is displaced out of contact with one or more of a plurality of individual workpieces secured within the tray. A malfunction sensor is secured to locations on each of the hydraulic lifts.

Other features associated with the tray include the provision of underside supports for mounting the tray upon a pair of spaced apart and parallel extending rails that facilitate the tray being reciprocated in a co-linear direction upon being actuated by an eccentric drive having a drive rod eccentrically secured at a first end to a motor driven and elongated component and at an opposite end to an underside location of the tray. An elongated (link) component further includes individual mounting locations for eccentrically mounting the drive rod so that a range of co-linear reciprocating actuation of the tray is established.

A processor/operating module is located upon the support surface and incorporates a number of functions including determining an amount of downwardly applied pressure (such as in lbs or kg) exerted against the reciprocating/orbiting tray mounted test pieces and varying a speed of a reciprocally driven tray upon which the test pieces are secured over a number of cycles/iterations to which the test pieces are subjected. The processor module further includes a readout display identifying an accruing number of iterations or cycles.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As previously described, the present invention discloses an abrasive wear testing machine, such as which incorporates gravity exerting weights or other type of fluid pressure applied/induced forces for downwardly biasing at least one abrading tool bits which arranged upon an underside of the overhead weighting and is exerted downwardly against one or more individual test pieces. The workpieces (or test pieces) are in turn being mounted within a supported tray which is then caused to reciprocally displace (in either opposite linear or eccentric/orbital fashion) upon a table top surface of the machine. A processor component determines an overall number of cycle (or iterations) in which the test piece securing tray is caused to displace and, in this fashion, the wear bit(s) abradingly engage each of the test pieces, this in order to determine wear characteristics over the specified number of displacement cycles.

Figure 1:
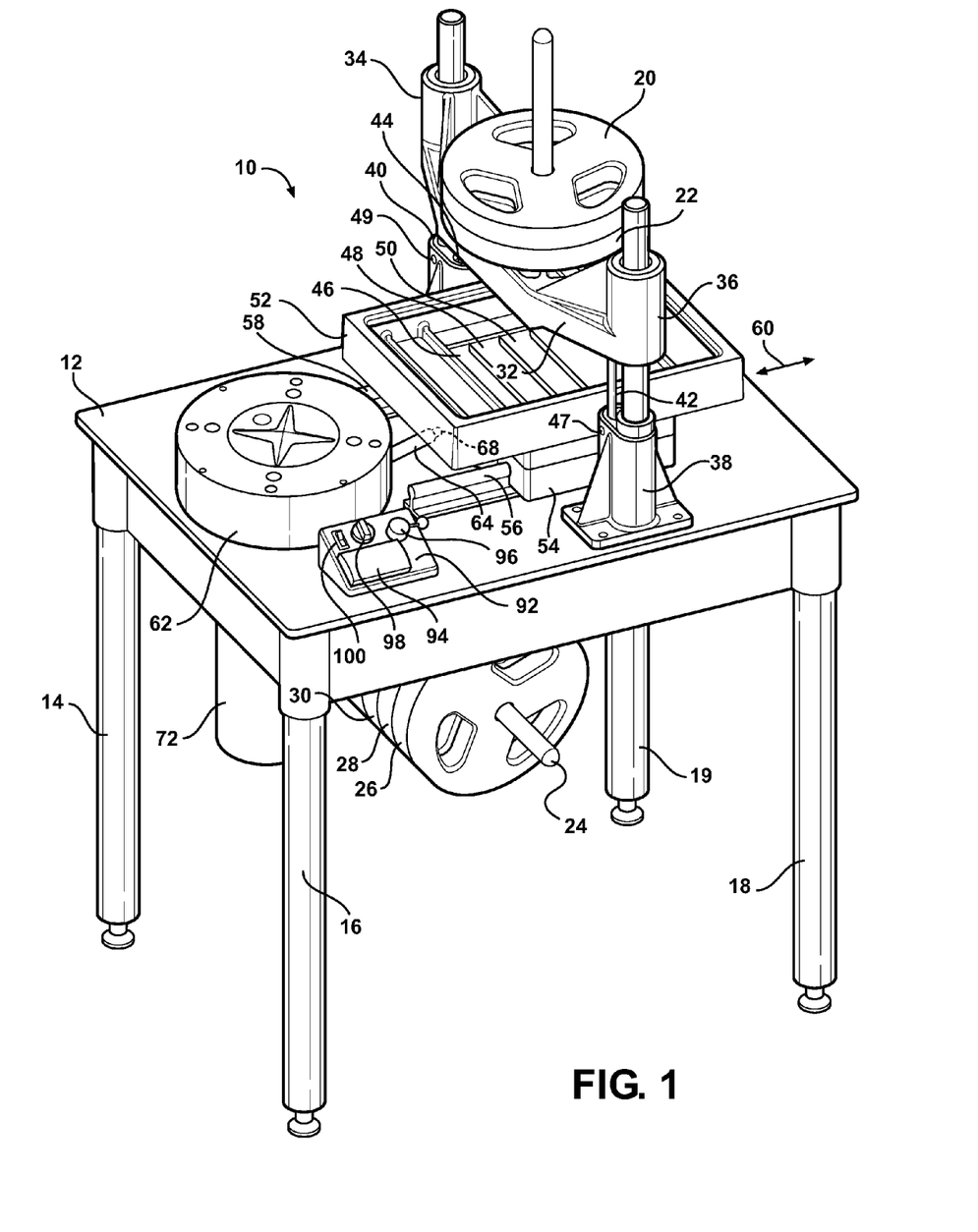
FIG. 1 is an operational view in perspective of the abrasive wear testing machine according to one preferred embodiment of the present inventions.

Referring first to FIG. 1, an operational view is shown in perspective at 10 of the abrasive wear testing machine according to one preferred embodiment of the present inventions. In this illustrated embodiment, the wear testing machine exhibits a table top surface 12, this being supported on a plurality of legs (three of which are shown at 14, 16, 18 with the fourth hidden from view in several of the views but shown at 19 in FIG. 2).

Load or weight application is provided by a plurality of free weights, see at 20 and 22 (as well as additional weights supported in stored fashion on a weight storing peg 24 extending underneath the table and as shown at 26, 28, 30, et. seq.). A bracket exhibits a central planar surface 32 with first and second vertical extending and interiorly channeled receiving ends 34 and 36. The bracket is configured so that the receiving channels 34 and 36 each are seatingly engaged in upwardly displaceable fashion upon a pair of upwardly extending hydraulic lifts, see 38 and 40.

Figure 2:
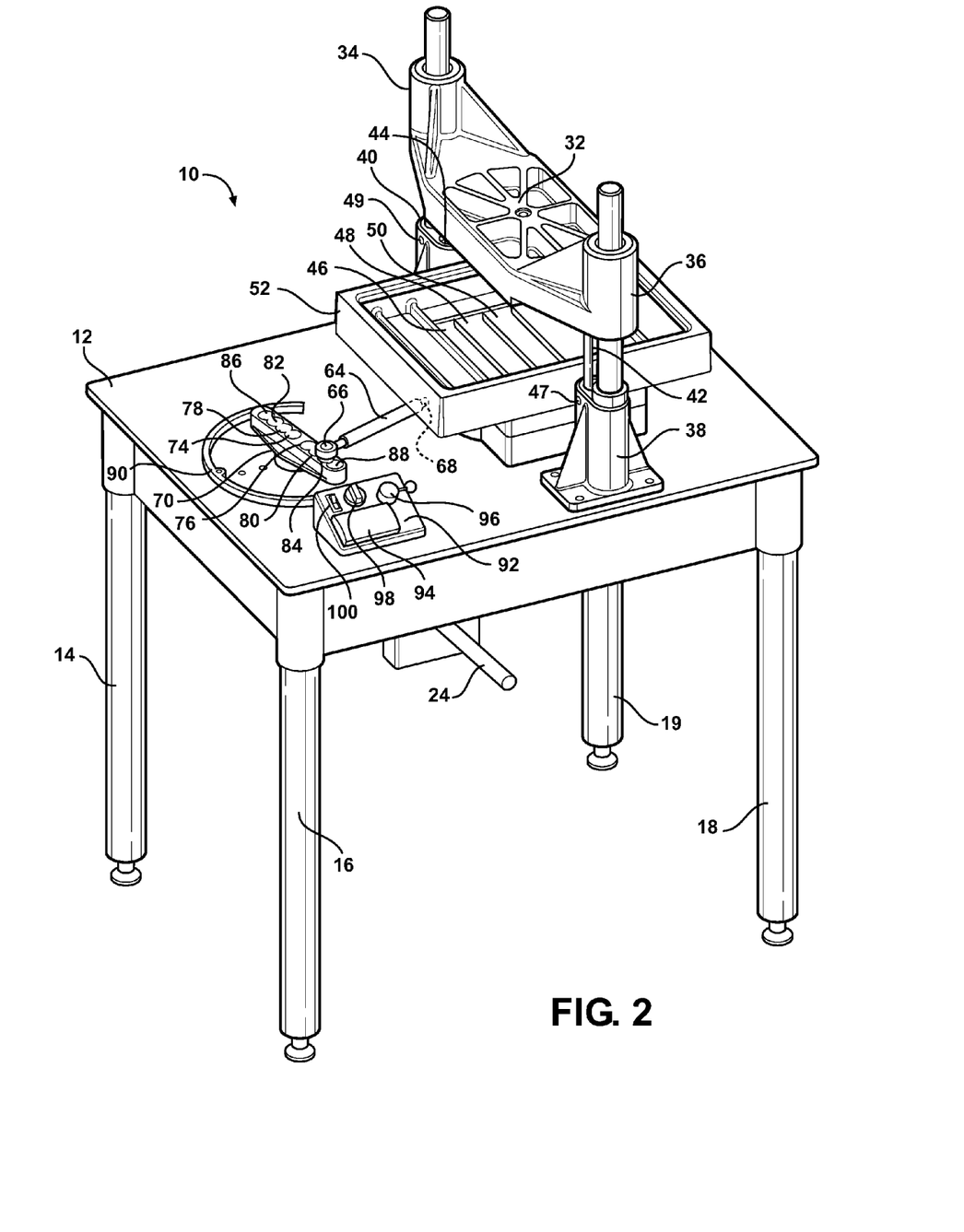
FIG. 2 is a successive illustration to that shown in FIG. 1, with certain elements removed for ease of illustration including such as the platform supported weights and eccentric drive cover, and further showing the manner in which the workpiece supporting tray is linearly and reciprocally traversed.

The lifts 38 and 40 each include a reverse and upwardly retracting drive arm, see as shown at 42 and 44, respectively, these cooperating to upwardly displace the weighted bracket such that its underneath mounted wear bit (the wear bit further not shown in FIGS. 1-4 but illustrated in detail in each of FIGS. 5 and 7) is displaced out of contact with one or more of a plurality of individual work-pieces (or test pieces), such as are further shown at 46, 48, 50, et. seq. in each of the represented views of FIGS. 1 and 2. Additional features include such as malfunction sensors, see at 47 and 49, and which are secured to locations on each of the hydraulic lift components 38 and 40 for determining an error in the operation of the hydraulic lift.

Although not shown, it is understood that any necessary hydraulic drive control and/or electrical input is provided for actuating the lifts 38 and 40, and so that any amount of downward weighting provided by the free weights is countered and the bracket 32 is caused to upwardly displace in a desired manner following completion of a desired wear testing program. It is also understood and envisioned that any other suitable electrical, hydraulic or mechanical input can be employed for establishing a desired servo controlling lift for retracting (upwardly raising) the weight stack and associated bracket, and beyond that specifically described herein.

Figure 5:
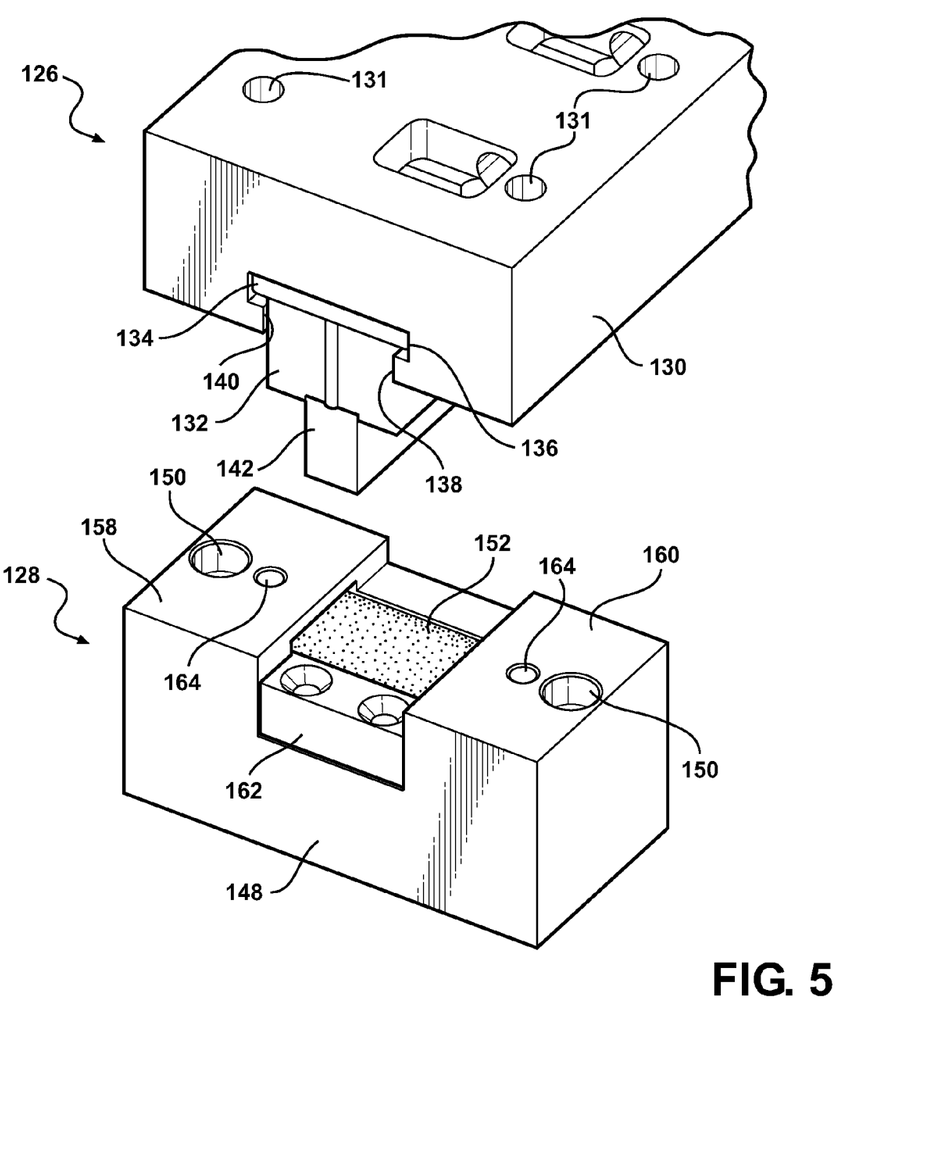
FIG. 5 is an exploded view of an upper tool part secured to the downwardly facing weighted surface and opposing a wear test piece secured within a lower jig tool part in secured to an inner tray location.
Figure 6:
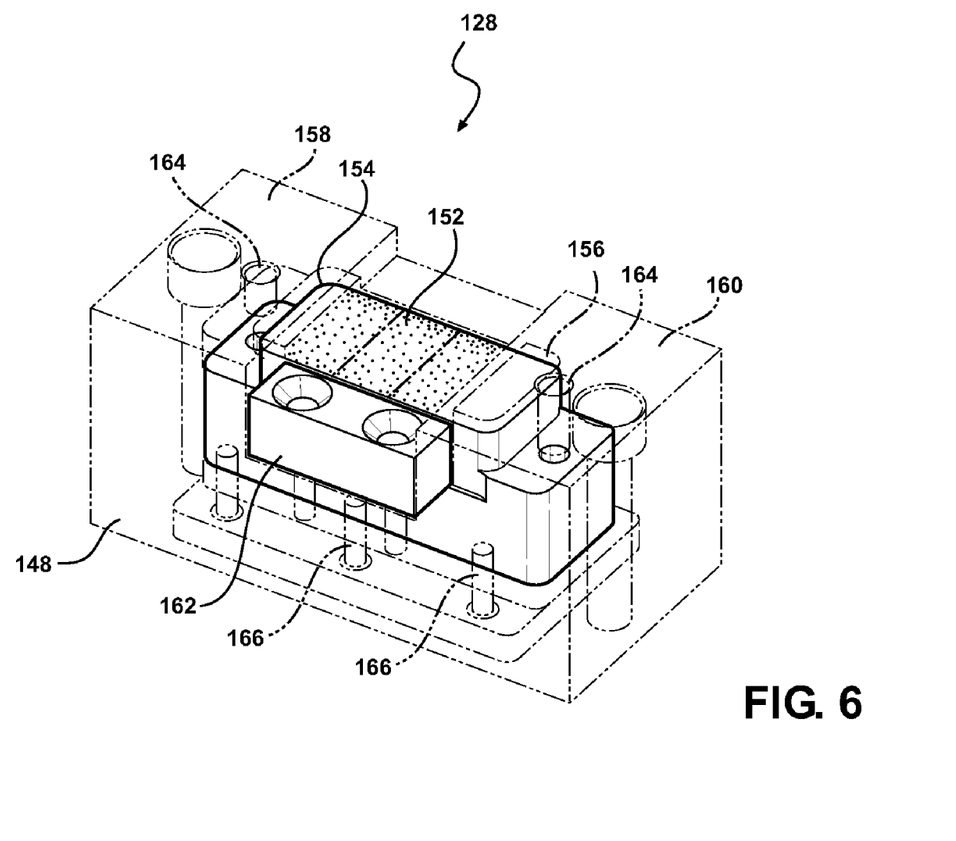
FIG. 6 is a succeeding perspective view of the lower tool part, also shown in FIG. 5, and in partially transparent fashion in order to further illustrate both the manner of securing the test piece within the lower jig, as well as of securing the jig to the tray surface location.

As will be further described in reference to FIGS. 5 and 6, the present invention further contemplates other variations of a lower tool part incorporating a wear or test piece (i.e. workpiece), and which can be utilized to microscopically analyze a wear profile of a given test piece material given such variables as an amount of applied weight, the material constitution of the downwardly secured and abrading tool bit, and the number of iterations/cycles of the abrading bit combined with the pathway or arc upon which the bits are traversed. Also shown in FIGS. 1 and 2 is a tray 52, this exhibiting an open and recessed interior within which the test pieces 46, 48, 50, et. seq., are mounted. The tray 52 is constructed such that the test pieces can be either dry mounted (with the addition of appropriate fastening jig hardware) or can be immersed within a desired fluid (e.g. water, oil-based fluid or the like) and so that a desired environment is created for wear testing of the test pieces. While the tray can be configured to support any plurality of test pieces, one desired variant allows for up to eighteen individual test blocks (as will be individually described in detail in FIGS. 5 and 6) to be secured within the open interior of the tray 52.

The variant of FIG. 1 illustrates the tray 52 as further including a pair of opposite side and underside extending supports (one of which is shown at 54 and the other hidden from view), each of which exhibiting an interior channel for mounting the tray upon a pair of spaced apart and parallel extending rails, see further at 56 and 58. In this fashion, the rails 56 and 58 facilitate the tray being reciprocated in a co-linear direction, see arrow 60, upon being actuated by an eccentric drive (see cover 62 in FIG. 1) which acts upon a drive rod 64 eccentrically secured at end 66 (see FIG. 2 in which cover 62 is removed) to the eccentric drive and further at opposite end 68 (as shown in phantom in FIG. 2) to an underside location of the tray 52.

The end connections 66 and 68 are such that they establish multi-axial articulating joints which, in one illustrated variant, may include at least one spherically shaped portion secured in upwardly extending fashion from an engagement location with the drive connection (see at 70 below), this permitting the drive rod to displace in multi-axial permitting fashion, and such as within an outer supporting collar integrally formed with an end of the rod 64. In this fashion, the eccentric linkage establishes the necessary drive parameters while at the same time accommodating any misalignments or eccentricities resulting from eccentric driving of the rod, thereby preventing the same from affecting the repeated reciprocation of the tray 52 over the desired number of iterations/cycles.

Figure 3:
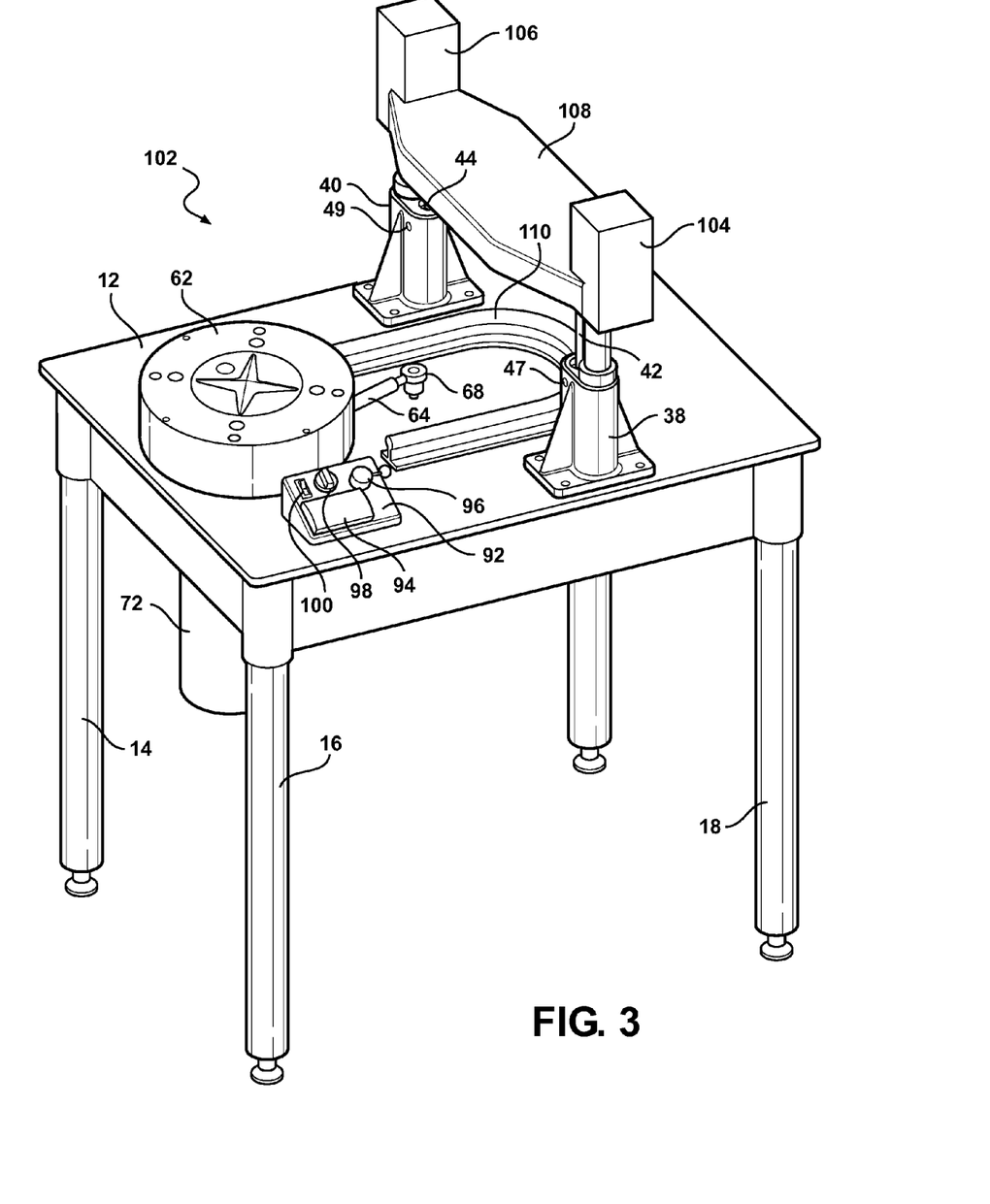
FIG. 3 is an alternate variant in comparison to that shown in FIG. 2, in which downwardly pressure exerting cylinders replace the free weights and further incorporating an alternately configured and eccentric drive track for reciprocating the workpiece supporting tray in multi-directional fashion along a two dimensional arc.
Figure 4:
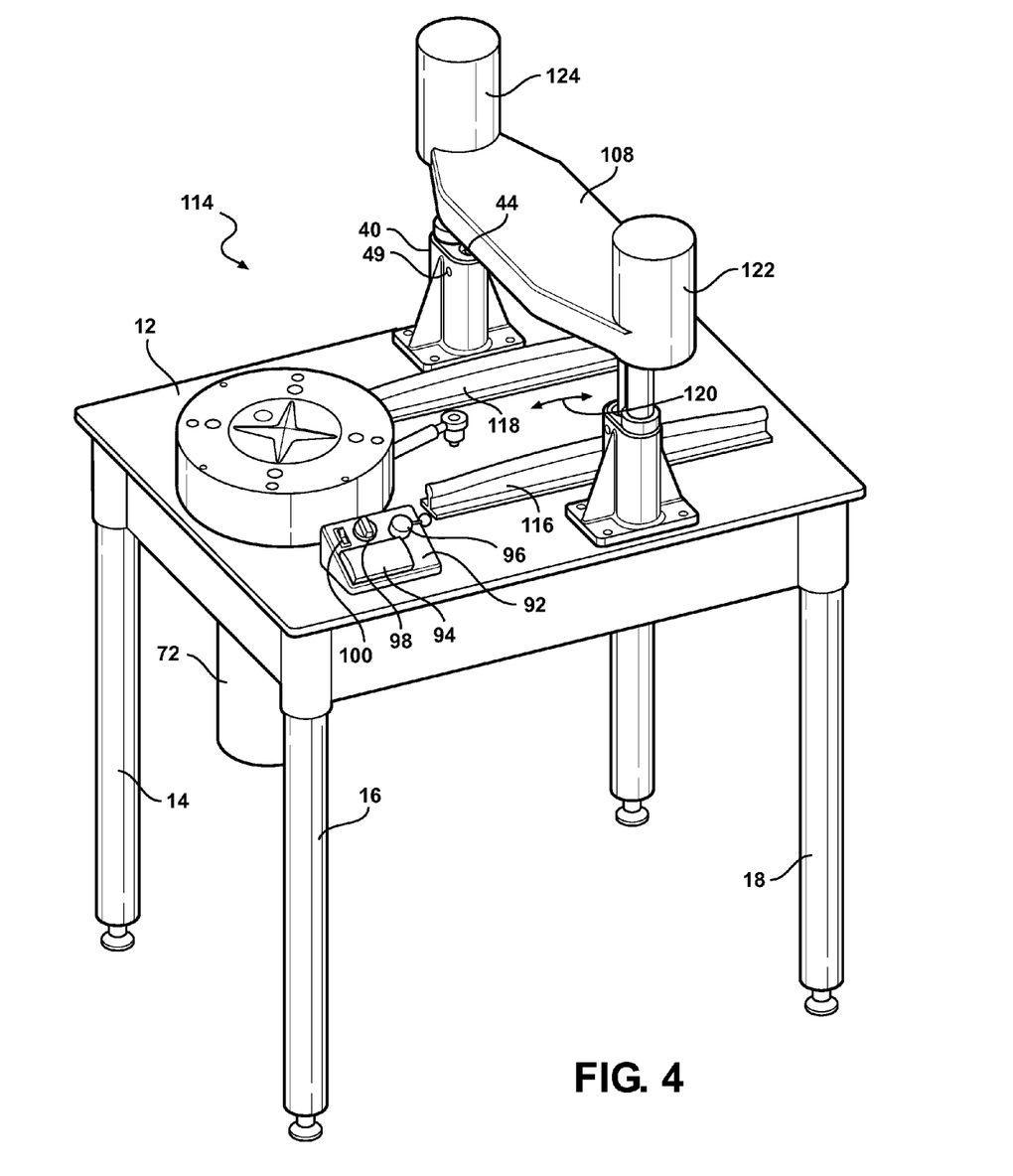
FIG. 4 is a modification of the variant in FIG. 3 in which a pair of three dimensional/elevating drive tracks are secured to the table top surface and, in combination with the reciprocally driven workpiece carrying tray, establish a multi-directional displacement along a three dimensional arc.

As again shown in FIG. 2, the removal of the eccentric drive cover 62 in FIG. 1 further illustrates the features of a motor rotated/driven and elongated component 70 (see also underside motor housing 72 in each of FIGS. 1, 3 and 4 for rotatably driving the component 70). The elongated (link) component includes a number of individual mounting locations for eccentrically mounting the illustrated end 66 of the drive rod 64, and so that the range of co-linear reciprocating actuation of the tray 52 is varied. Specifically, releasably securing eccentric drive rod end 66 to each of the identified locations 74, 76, 78, 80, 82, 84, 86 and 88 in the rotating link establishes a corresponding linear stoke ranging from one up to eight inches. Also shown at 90 in FIG. 2 is a guide template for receiving the eccentric drive cover 62 in mounting fashion over the rotating link 70, the cover exhibiting an arcuate window (not shown) along an inner facing side through which extends the drive rod 64 and in order to provide clearance for its eccentric stroke.

A processor/operating module 92 is located upon the table top surface 12 and which includes a number of functions such as determining an amount of downwardly applied pressure (such as in lbs or kg) exerted against the reciprocating/orbiting tray secured test pieces, as well as the speed of reciprocally driven tray and the number of cycles/iterations to which the test pieces mounted in the tray are subjected. A readout display is illustrated at 94 (such as also identifying an accruing number of iterations or cycles), with additional components including those shown at 96 for providing for such as an up/down actuation of the cylinder retracted weighted bracket, at 98 for the speed of the eccentric drive (in one non-limiting example approaching a range of approximately 90 cycles per minute), and at 100 for switching the machine on or off. Although not shown, additional functionality of the processor module provides for entering (such as through the use of an appropriate keypad) a desired number of cycles, as well as reset and/or modification means for changing a program after it has been initiated.

In operation of the wear testing machine in the variant of FIGS. 1 and 2, the underside mounted and positioned upper tool part (this including the wear bit of FIGS. 5 and 7) is exerted against a selected test piece mounted within a lower part in turn secured in jig fashion within the open tray 52. The wear pieces can include any suitable material of an abrading nature, such as selected from titanium, other metals, ceramics, plastics or the like and in which it is desirous to mimic how a given material responds to placement within a specified dynamic environment.

FIG. 2 is again a successive illustration to that shown in FIG. 1, with certain elements removed for ease of illustration and including such as the platform supported weights and eccentric drive cover. In this fashion, FIG. 2 likewise illustrates the manner in which the workpiece supporting tray is linearly and reciprocally traversed.

Referring now to FIG. 3, an alternate variant is shown at 102 in comparison to that shown in FIG. 2, in which downwardly pressure exerting cylinders, these being illustrated at 104 and 106 and which are integrally incorporated into a bracket shown at 108 which is supported upon the upwardly projecting shaft portions of the drive cylinders 38 and 40. The pressure cylinder configuration can be influenced by a suitable pressurized input (such as arranged underneath the table or remotely connected through an appropriate pressure resistant conduit) and which replaces the free weights in FIGS. 1 and 2.

The arrangement of FIG. 3 further incorporates an alternately configured and eccentric drive track 110 for reciprocating the work-piece supporting tray (not shown in this illustration) in multi-directional fashion along a two dimensional arc. Although not shown, it is also understood that the drive track 110 can be modified to form a closed and continuous loop, such as exhibiting any of a circular, oval or elliptical shape.

Referring to FIG. 4, a modification 114 of the variant in FIG. 3 is provided in which a pair of three dimensional/elevating drive tracks, see at 116 and 118, are secured to the table top surface 12 and, in combination with a reconfigured underside associated with a reciprocally driven workpiece carrying tray (not shown) such as in order to permit the tray to displace both horizontally and vertically along each linear stroke, thereby establishing a multi-directional (see arrow indication 120) displacement along a three dimensional arc. FIG. 4 also shows modified drive cylinders 122 and 124, these optionally operating under any of pneumatic (air), other hydraulic or servo-electric inputs, and in order to exert a desired downward force of its underside located wear bits (not shown) in biasing contacting and abrading fashion against the individual test pieces (also not shown).

Figure 7:
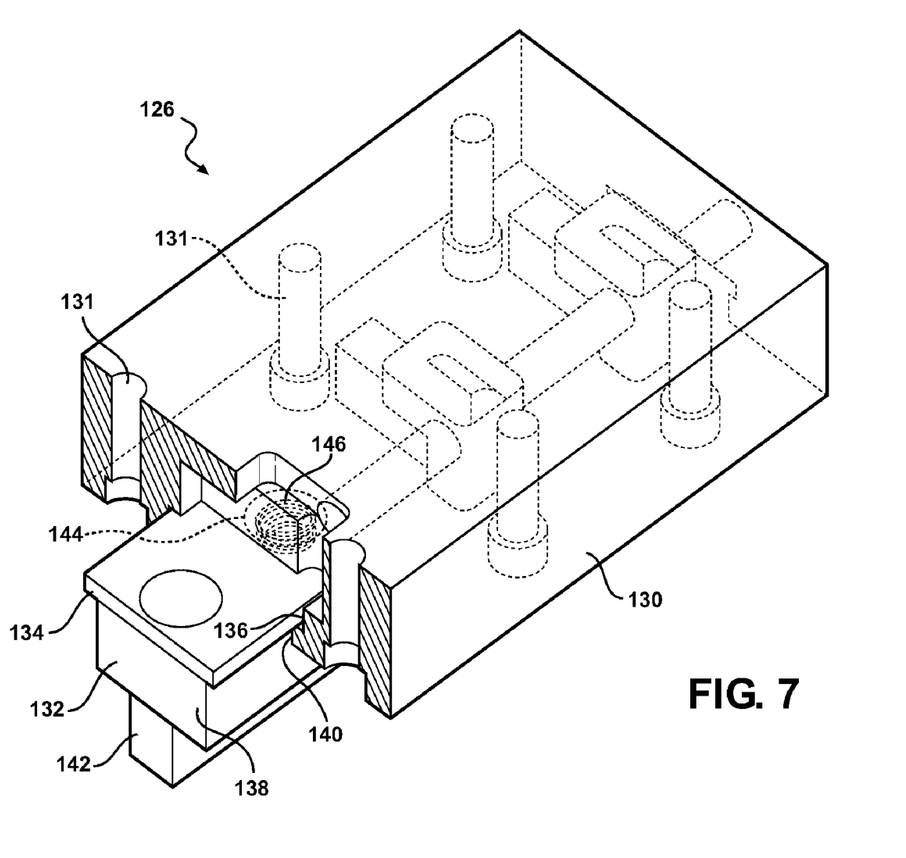
FIG. 7 is a likewise partially transparent illustration of the upper tool part and further showing features including individual spring loading of each wear abrading piece/bit (this in order to compensate for individual misalignments owing to different wear characteristics of the test pieces) and in addition to an underside communicable receiving track profile for lengthwise mounting of individual abrading bits in fixed downwardly extending fashion.

Finally, FIGS. 5-7 collectively illustrate a succession views of an upper tool part 126 and a lower tool part 128, and which are incorporated into the wear testing machine according to any of the previously described embodiments. In particular, and as previously discussed, the upper tool part 126 includes a three dimensional rectangular shaped body 130 (such as constructed of a durable grade steel or other appropriate material) and which is secured by such as suitable fasteners inserting through apertures 131 defined through the body 130 for securing the same to an underside location of the downwardly displaceable weight stack (or pressure activated platform).

As also shown in FIG. 6, the upper tool part 126 includes one or more intermediate holder bodies, see at 132, these being configured to include a modified three dimensional body and exhibiting an upper most positioned outward ledge portion, at 134. In this fashion, the holder body 132 may be mounted in an linearly inserted and secured fashion within a mating end communicable and likewise linear extending profile defined within the interior of the upper tool part and in communication with its lower face (see as further shown by recess located and linearly extending undercut 136 formed in communication with inner facing and bottom surface communicable walls 138 and 140.

This aligning and undercut guide established relationship allows for secure and sliding engagement of the individual wear bit holder bodies 132 in downwardly facing fashion within the upper tool part 126, and further such that the body 132 is prevented from undesirable displacement (e.g. including rocking) relative to the three dimensional body 130 within which it is secured. Although not clearly shown, it is understood that the individual tool holder bodies 132 are engaged at specified linear positioned locations along the lengthwise extending underside of the upper tool part. As will be described subsequently, the dimensioning of the upper tool part can further be such that a plurality (such as of three) individual tool holding bits can be secured within its channeled underside in a fixed and misalignment-preventative fashion.

A wear bit is shown at 142 and can again include such as a titanium or other suitable wear inducing material. The wear bit 142 can also be alternately configured and is engaged within an underside (and downward looking) location of the holder body 132. Further shown at 144 in FIG. 7 is a further center line located seating aperture, this defined in an upper surface of the upper tool part 126, and which is in communication with the location of the holder body 132 and individually held tool bit 142.

The manner of securing the tool bit 142 within the holder body 132 is further such that it can be vertically displaced relative thereto, the holder body 132 further being open through an aligning top location with the aperture 144 and such that a force exerted from a coil spring 146 seated within the aperture 144 downwardly presses on the wear bat 142 (in one variant exerting a 60 lb pressure force), influencing the same into constant contact with the bit 142. As shown in the phantom underside of FIG. 7, provision in made in the upper tool part 126 for receiving up to two additional (totaling three) wear bits, such as singularly shown at 142, along with additional and associated holding bodies 132.

In this fashion, multiple mounted tool holders with associated bits can abrade a corresponding plurality of lower tool part mounted wear bits (as will be described in FIGS. 5 and 6). The ability to individually and independently spring load each of the holder bodies 132 (and associated tool bits 142) compensates for any relative misalignment between multiple upper tool bit bodies, and which can result from uneven wear of the work-pieces (this in particular being in issue when work-piece wear bits of different material properties are employed in a given operation and which are abraded by individual tool bits contained within a common upper part 126.

As again shown in each of FIGS. 5 and 7, the lower tool part (or lower jig component) 128 may be constructed of a material similar to that used in the upper tool part 126 and may further exhibit a three dimensional and rectangular shaped body secured at an inner tray location (see again at 52 in FIG. 1) by such as jig mounting fasteners (not shown) engaging through apertures 150 extending through the lower tool part 128 and which align with additional mounting apertures (also not shown) defined in the upper surface of the tray interior.

As additionally shown in the partially transparent view of FIG. 6, a work-piece (or wear piece) 152 is provided and which is configured with rounded or like formed edges 154 (again FIG. 6) such that the piece 152 seats within a mating configured pocket 156 defined in the lower tool part body 148 for fixedly securing the same. The wear piece 152 can exhibit any desired material properties, and is often provided as a hybrid (composite) of any of a plastic/metal/ceramic and/or other material (see as generally illustrated by phantom designated portions), it being desired to be able to effectively gauge the wear properties of the sample material in order to determine its suitability for given dynamic applications.

The upper surface of the lower tool part body 148 is also elevated at ends 158 and 160, this in order to provide the necessary superstructure for mounting and securing the wear piece 152. Also shown at 162 is a laterally immobilizing jig secured component, this securing along a side location of the wear piece 152 in order to prevent misaligning movement of the same. Other features include additional jig securing apertures, see at 164, these corresponding to communicating surfaces associated with an interior supporting structure of the lower too part positioned underneath the wear bit 154 (see 164), as well as additional clamping locations 166 (see further FIG. 6).

The dimensioning of the lower tool (jig) part 128 is further such that a total of such as nine or eighteen parts 128 can be clamped onto the upper facing surface of the displaceable tray. Referencing again the opposing relationship established between the upper and lower tool parts in FIG. 5, the wear piece 152 can be positioned such that a central portion thereof (as shown in FIG. 6) aligns with the abrading contact location of a downwardly extending tool bit 142 associated with a corresponding upper tool part.

An operation protocol includes pre-measuring a wear piece 152 (such as microscopically) and prior to mounting the slide shaped piece 152 in the lower tool part in the illustrated fashion. The microscopic pre-measurement is provided as a basis measurement to determine a subsequent amount of abrading wear on the test piece 152 (and such as exerted by the downwardly facing, weighted, and fixedly positioned bit relative to the central wear piece zone and upon the plurality of lower jig mounted workpieces being reciprocated in the two and/or three dimensional reciprocating fashion).

Upon completing a desired operation, corresponding to a number of reciprocating cycles exerted on the workpiece supporting tray, each of the workpiece slides are removed and are again microscopically measured to determine the degree of wear of the specified abrasion zone. In this fashion, the present invention provides an efficient, effective and less costly mechanism for providing highly accurate wear assessment of a work-piece, with varying parameters for (downward) application force, direction of reciprocation (both two and three dimensional) of the supporting tray, and number of iterations/cycles of the various wear pieces.

Having described my invention, other and additional preferred embodiments will become apparent to those skilled in the art to which it pertains, and without deviating from the scope of the appended claims.

I claim:

1. An abrasive wear testing machine, comprising:
   a support surface upon which is dynamically supported a tray, at least one wear piece being adapted to being secured upon said tray;
   said tray further comprising underside supports for mounting said tray upon a pair of spaced apart and parallel extending rails that facilitate said tray being reciprocated in a co-linear direction upon being actuated by an eccentric drive; and
   a tool bit supported in a fixed and downward load applied fashion against the wear piece;
   said tray being reciprocated a selected number of cycles to determine a wear profile exerted upon the wear piece by said tool bit.

2. The invention as described in claim 1, further comprising a vertically displaceable and weight supporting bracket to which said tool bit is secured, said bracket configured so that end located receiving channels are each seatingly engaged upon upwardly extending hydraulic lifts secured to the support surface.

3. The invention as described in claim 2, further comprising a plurality of free weights arranged upon the hydraulic lifts.

4. The invention as described in claim 2, said lifts each further comprising a reverse and upwardly retracting drive arm, these cooperating to upwardly displace the weight supporting bracket such that its underneath mounted bit is displaced out of contact with one or more of a plurality of individual wear pieces secured within said tray.

5. The invention as described in claim 4, further comprising a malfunction sensor secured to locations on each of said hydraulic lifts.

6. The invention as described in claim 1, said eccentric drive further comprising a drive rod eccentrically secured at a first end to a motor driven and elongated component and at an opposite end to an underside location of the tray.

7. The invention as described in claim 6, said elongated component further comprising a number of individual mounting locations for eccentrically mounting said drive rod so that a range of co-linear reciprocating actuation of the tray is established.

8. The invention as described in claim 1, further comprising a processor/operating module located upon said support surface and which includes a number of functions including at least one of determining an amount of downwardly applied pressure (such as in lbs or kg) exerted against the reciprocating/orbiting tray secured wear pieces and varying a speed of a reciprocally driven tray and a number of cycles/iterations to which the wear pieces mounted in the tray are subjected.

9. The invention as described in claim 8, said processor module further comprising a readout display identifying an accruing number of iterations or cycles.

10. The invention as described in claim 1, further comprising a vertically displaceable bracket to which said tool bit is secured, said bracket exhibiting first and second end-mounted and downwardly pressure exerting cylinders.

11. The invention as described in claim 1, said tray further comprising underside supports for mounting upon an eccentric drive track for reciprocating the wear piece supporting tray in multi-directional fashion along a two dimensional arc.

12. The invention as described in claim 1, said tray further comprising underside supports for mounting upon a pair of three dimensional/elevating drive tracks secured to said support surface to displace said tray both horizontally and vertically in multi-directional fashion.

13. The invention as described in claim 2, said tool bit being secured to an underside extending location of an upper tool part, which is in turn mounted to said vertically displaceable and weight supporting bracket.

14. The invention as described in claim 13, said upper tool part further comprising one or more intermediate holder bodies, each of which are configured to include a modified three dimensional body and exhibiting an upper most positioned outward ledge portion, said holder bodies being mounted in a linearly inserted and secured fashion within a mating end profile of said upper tool part extending within a lengthwise interior and in communication with its lower face.

15. The invention as described in claim 14, said tool bit being engaged within an underside facing location of said intermediate holder body such that it can be vertically displaced relative thereto, said holder body further being open through an aligning top location with an aligning aperture within said upper tool part for seating therein a coil spring, said spring exerting a continuous and downward force upon said tool bit.

16. The invention as described in claim 13, further comprising a lower tool part secured at an inner tray location in opposing fashion to said upper tool part, said wear piece seating within a mating configured pocket defined in a body of said lower tool part.

17. An abrasive wear testing machine, comprising:
a support surface upon which is dynamically supported a tray, at least one wear piece adapted to being secured upon said tray;
underside supports for mounting the tray upon a pair of spaced apart and parallel extending rails that facilitate the tray being reciprocated in a co-linear direction upon being actuated by an eccentric drive;
a tool bit supported in a fixed and downward load applied fashion against the wear piece; and
a vertically displaceable and weight supporting bracket to which said tool bit is secured, said bracket configured so that end located receiving channels are each seatingly engaged upon upwardly extending lifts secured to the support surface;
the tray being reciprocated a selected number of cycles to determine a wear profile exerted upon the wear piece by said tool bit.

18. The invention as described in claim 17, further comprising a processor/operating module located upon said support surface and which includes a number of functions including at least one of determining an amount of downwardly applied pressure (such as in lbs or kg) exerted against the reciprocating/orbiting tray secured test pieces and varying a speed of a reciprocally driven tray and a number of cycles/iterations to which the test pieces mounted in the tray are subjected.

19. The invention as described in claim 17, said lifts each further comprising a reverse and upwardly retracting drive arm, these cooperating to upwardly displace the weight supporting bracket such that its underneath mounted bit is displaced out of contact with one or more of a plurality of individual wear pieces secured within said tray.

20. An abrasive wear testing machine, comprising:
a support surface upon which is dynamically supported a tray, at least one wear piece adapted to being secured upon said tray; and
a tool bit supported in a fixed and downward load applied fashion against the wear piece;
a vertically displaceable and weight supporting bracket to which said tool bit is secured, said bracket configured so that end located receiving channels are each seatingly engaged upon upwardly extending hydraulic lifts secured to the support surface;
said tool bit being secured to an underside extending location of an upper tool part, which is in turn mounted to said vertically displaceable and weight supporting bracket;
a lower tool part secured at an inner tray location in opposing fashion to said upper tool part, said wear piece seating within a mating configured pocket defined in a body of said lower tool;
the tray being reciprocated a selected number of cycles to determine a wear profile exerted upon the wear piece by said tool bit.

21. An abrasive wear testing machine, comprising:
a support surface upon which is dynamically supported a tray, at least one wear piece adapted to being secured upon said tray; and
a tool bit supported in a fixed and downward load applied fashion against the wear piece;
a vertically displaceable and weight supporting bracket to which said tool bit is secured, said bracket configured so that end located receiving channels are each seatingly engaged upon upwardly extending hydraulic lifts secured to the support surface;
said lifts each further comprising a reverse and upwardly retracting drive arm, these cooperating to upwardly displace the weight supporting bracket such that its underneath mounted bit is displaced out of contact with one or more of a plurality of individual wear pieces secured within said tray;
a malfunction sensor secured to locations on each of said hydraulic lifts;
the tray being reciprocated a selected number of cycles to determine a wear profile exerted upon the wear piece by said tool bit.

22. An abrasive wear testing machine, comprising:
a support surface upon which is dynamically supported a tray, at least one wear piece being adapted to being secured upon said tray;
said tray further comprising underside supports for mounting upon an eccentric drive track for reciprocating the wear piece supporting tray in multi-directional fashion along a two dimensional arc; and
a tool bit supported in a fixed and downward load applied fashion against the wear piece;
said tray being reciprocated a selected number of cycles to determine a wear profile exerted upon the wear piece by said tool bit.

23. An abrasive wear testing machine, comprising:
a support surface upon which is dynamically supported a tray, at least one wear piece being adapted to being secured upon said tray;
said tray further comprising underside supports for mounting upon a pair of three dimensional/elevating drive tracks secured to said support surface to displace said tray both horizontally and vertically in multi-directional fashion; and
a tool bit supported in a fixed and downward load applied fashion against the wear piece;
said tray being reciprocated a selected number of cycles to determine a wear profile exerted upon the wear piece by said tool bit.

* * * * *